United States Patent [19]

Argoud et al.

[11] Patent Number: 4,658,411
[45] Date of Patent: Apr. 14, 1987

[54] GONIOMETRIC DEVICE PARTICULARLY FOR X-RAY OR NEUTRON DIFFRACTOMETRY ON MONOCRYSTALS OR ANY OTHER SAMPLE

[75] Inventors: Roger Argoud, Saint-Egreve; Jean-Noël Muller, Seyssinet Pariset, both of France

[73] Assignee: Centre National de la Recherche Scientifique (CNRS)., Paris, France

[21] Appl. No.: 746,548

[22] Filed: Jun. 19, 1985

[30] Foreign Application Priority Data

Jun. 22, 1984 [FR] France .................. 84 09846

[51] Int. Cl.⁴ .................. G01N 23/20
[52] U.S. Cl. .................. 378/81; 250/390; 250/442.1; 378/80
[58] Field of Search ........ 378/81, 80, 71; 356/31; 250/390 H, 442.1, 453.1

[56] References Cited

U.S. PATENT DOCUMENTS 4,016,420 4/1977 Rieder .................. 378/77
4,263,510 4/1981 Ciccarelli et al. .................. 378/46

FOREIGN PATENT DOCUMENTS 1133153 7/1962 Fed. Rep. of Germany .

OTHER PUBLICATIONS

"Apparatus Based on Phillips PW 1100 Diffractometer for Crystal-Structure Research at High Pressures", W. Denner and Heinz Schulz, *Philips Tech Rev.* 38, pp. 246-253, 1978/79, No. 9.
S. Samson, E. Goldish and C. J. Dick, "A Novel Low-Temperature X-ray Goniometer with Closed-Cycle Cooling to about 18K" *J. Appl. Cryst.* vol. 13, (1980), pp. 425-432.

*Primary Examiner*—Janice A. Howell
*Assistant Examiner*—Constantine Hannaher
*Attorney, Agent, or Firm*—Sandler & Greenblum

[57] ABSTRACT

A goniometric device particularly for X-ray or neutron diffractometry on monocrystals or any other sample comprises a sample-holder to maintain the monocrystal to be analyzed in the axis of the incident X-ray or neutron beam. Means for driving this sample-holder on itself, about a first axis, and also in rotation about a second axis perpendicular to the first and a third axis perpendicular to the second. The sample-holder is borne by a slave-goniometer comprising a transverse bar made of ferromagnetic material fast with the sample-holder, therefore perpendicular to the first axis of rotation of the sample-holder on itself. The sample-holder is rotatably mounted onto a support forming part of a universal joint mounted on a fixed base and of which the two perpendicular axes correspond respectively to the second and third axes of rotation. Means are provided for creating a magnetic field whose orientation varies in space so that, for each determined orientation of the magnetic field, the ferromagnetic bar and consequently the sample-holder and the monocrystal take this same orientation.

14 Claims, 6 Drawing Figures

GONIOMETRIC DEVICE PARTICULARLY FOR X-RAY OR NEUTRON DIFFRACTOMETRY ON MONOCRYSTALS OR ANY OTHER SAMPLE

BACKGROUND OF THE INVENTION

The present invention relates to a goniometric device particularly for X-ray or neutron diffractometry on monocrystals or any other sample.

Diffractometers known at the present time for the study of monocrystals by X-ray analysis, are of the "four circles" or derived type and they allow the displacement of the monocrystal in rotation about three axes concurrent at the same point. This monocrystal is generally mounted on a sample-holder mobile in rotation about a first axis, of angle $\phi$, this sample-holder is in turn mounted on an inner circle itself mounted to rotate inside an outer circle, about a second axis perpendicular to the first, of angle $\chi$, and finally the outer circle is mounted to rotate about a third vertical axis which is the axis of the goniometer, the outer circle rotating about this third axis of angle $\omega$. Although generally suitable for studying monocrystals in the open air, such diffractometers are not adapted to the study of the properties of these monocrystals housed inside a tight enclosure.

It is an object of the present invention to remedy these drawbacks by providing a device for making the measurement on monocrystals or other sample placed inside a tight enclosure, with very high precision, in the lack of any control goniometer.

To this end, this goniometric device particularly for X-ray or neutron diffractometry on monocrystals or any other sample comprising a sample-holder to maintain the monocrystal to be analyzed in the axis of the incident X-ray or neutron beam, means for driving this sample-holder on itself, about a first axis, and also in rotation about a second axis perpendicular to the first and a third axis perpendicular to the second, is characterized in that the sample-holder is borne by a slave-goniometer comprising a transverse bar made of ferromagnetic material fast with the sample-holder, therefore perpendicular to the first axis of rotation of the sample-holder on itself, a support on which the sample-holder is rotatably mounted and which forms part of a universal joint mounted on a fixed base and of which the two perpendicular axes correspond respectively to the second and third axes of rotation, and means are provided for creating a magnetic field whose orientation varies in space so that, for each determined orientation of the magnetic field, the ferromagnetic bar and consequently the sample-holder and the monocrystal take this same orientation. Perpendicular is understood to mean that fact that two axes form together an angle of 90° or slightly different.

The means creating the magnetic field whose orientation varies in space may be constituted by a permanent magnet mounted to rotate on itself about the first axis and which replaces the conventional goniometric head.

According to a variant embodiment of the invention, the means creating the magnetic field with space-variable orientation are constituted by an assembly of coils disposed around the slave-goniometer and having currents of adjustable intensities passing therethrough, the elementary magnetic fields created by the different coils contributing to form a resultant magnetic field of variable orientation which controls the positon of the sample-holder.

The goniometric device according to the invention offers the advantage that, due to the use of a magnetic coupling for obtaining servo-control of the position of the sample-holder, it is possible to isolate the sample-holder and the monocrystal subjected to the study from the outside by means of a tight enclosure. It is thus possible to make measurements at very low temperatures, by housing the slave-goniometer inside a cryostat. Measurements may also by made in a gaseous environment other than air, in an enclosure with controlled hygrometric degree or in which a pressure prevails which differs from atmospheric pressure (vacuum or pressure of several tens of bars).

Thanks to a judicious choice of the materials constituting the goniometric device and of the pivots chosen to allow the movements of rotation, it is possible to obtain, with the goniometric device, a precision of positioning of the order of 0.005°.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 1:
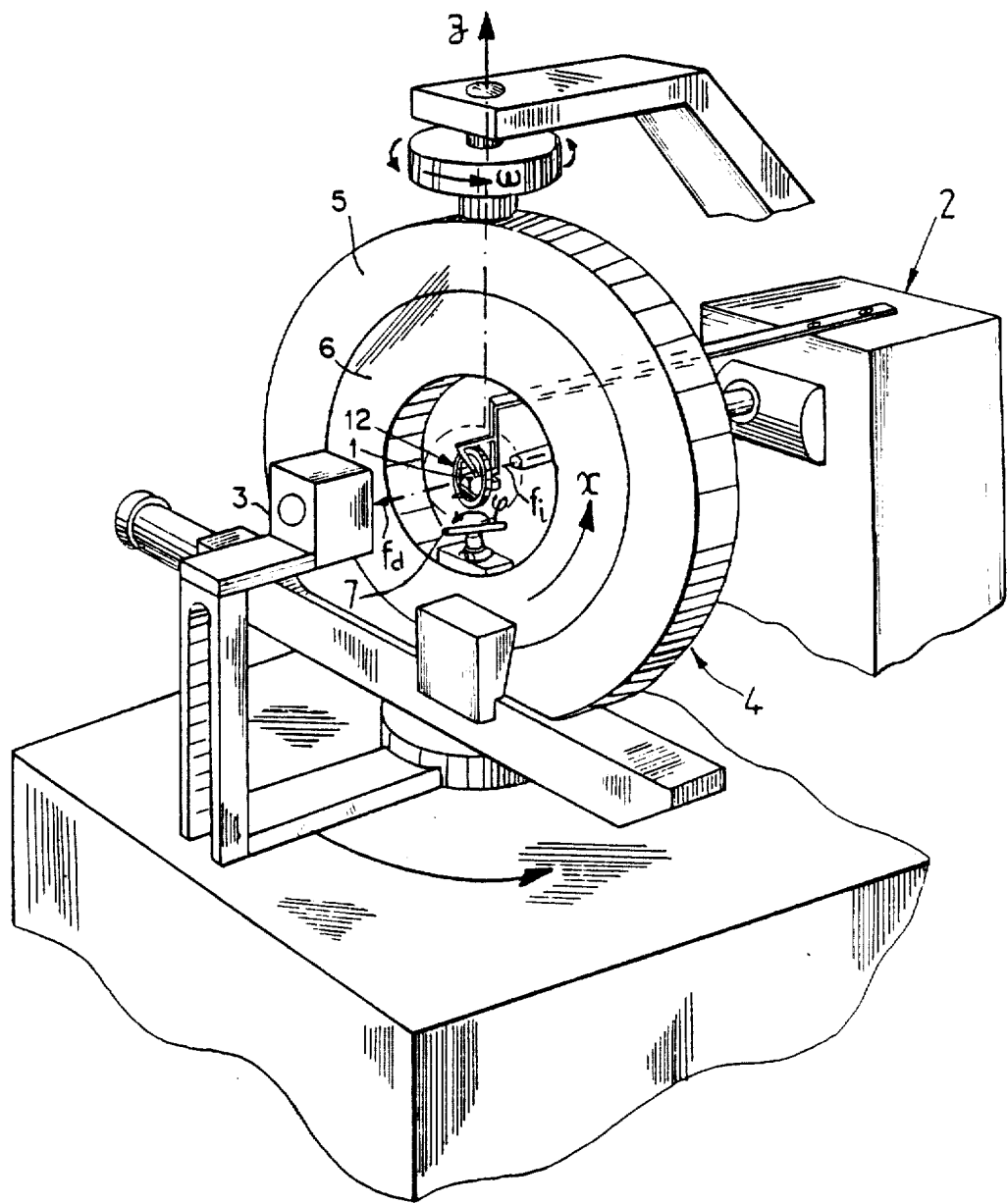
FIG. 1 is a perspective view of a diffractometer equipped with a goniometric device according to the invention.
Figure 2:
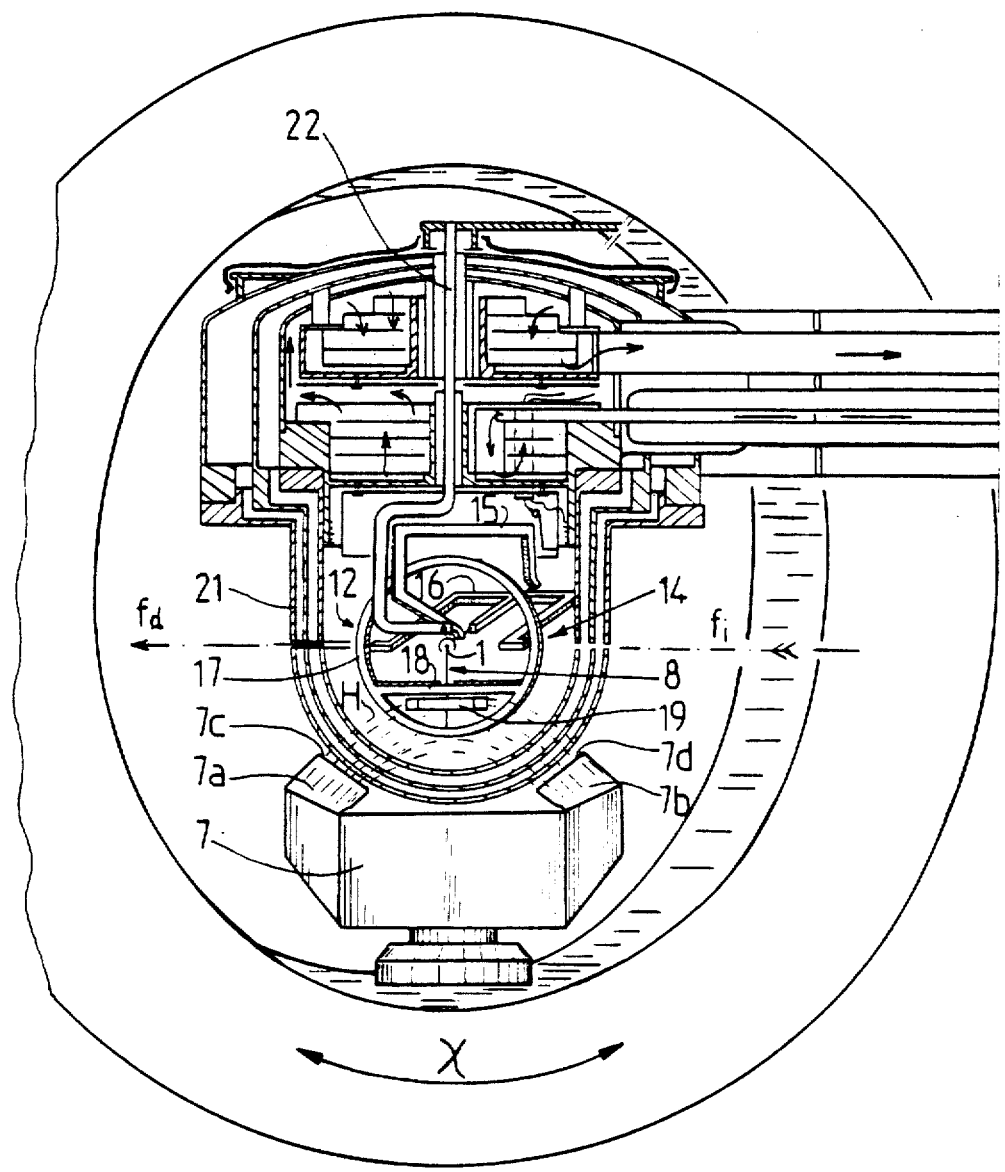
FIG. 2 is a perspective view, at a larger scale, of a goniometric device according to the invention applied to the study, by X-ray analysis, of a monocrystal contained in a cryostat.

The goniometric device according to the invention which is shown in FIGS. 1 and 2, is intended for the study of a monocrystal 1 on which falls an incident beam fi of X-rays coming from an X-ray emitter 2 and from which issues a diffracted beam $f_d$ picked up by a detector 3.

The goniometric device employs a control goniometer 4 comprising an outer circle 5, mobile about a vertical axis Oz, of angle $\omega$. Inside this circle 5 is housed another, coaxial circle 6 adapted to rotate on itself about its axis, of angle $\chi$. Furthermore, this inner circle 6 bears, on its inner cylindrical surface, a bar magnet 7 or master magnet which is mounted in place of the conventional goniometric head. This bar magnet or master magnet 7 is mounted to rotate on itself about a radial axis and it may thus rotate by an angle $\phi$.

Figures 3, 4, 5, 6:
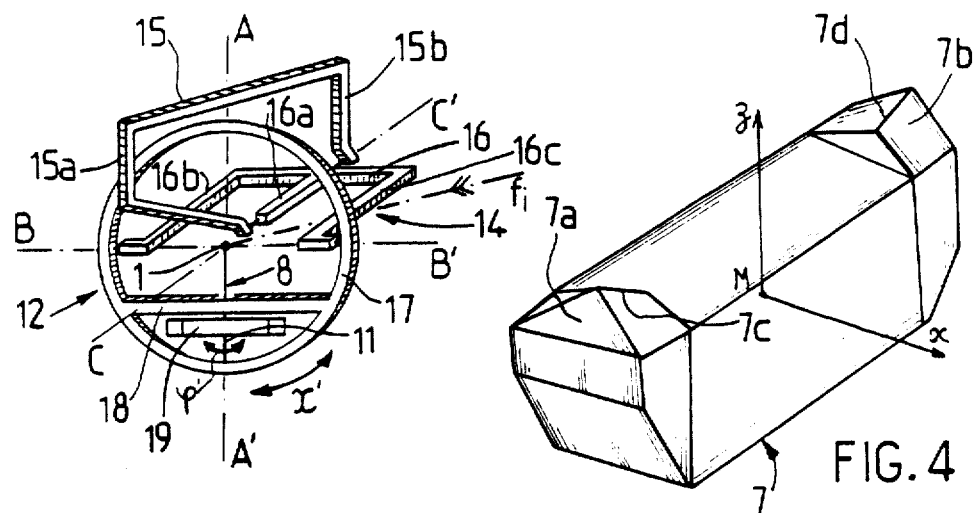
FIG. 3 is a perspective view of an embodiment of a slave-goniometer.supporting the monocrystal.
FIG. 4 is a perspective view of an embodiment of a master magnet included in the control goniometer.
FIG. 5 is a block diagram illustrating the movements around the various axis of rotation.
FIG. 6 is a vertical longitudinal sectional view, at a larger scale, of the upper part of the sample-holder.

The monocrystal 1 is fast with the upper end of a sample-holder 8 shown in detail in FIG. 6. This Figure shows that the monocrystal 1 is stuck on the upper end of a quartz rod 9 itself threaded in a tube 10 filled with silicon grease. The tube 10 is in turn screwed on the threaded upper end part of a rod 11 materializing the first axis of rotation AA' of the sample-holder 8 and of the monocrystal 1 on themselves. This assembly makes it possible to adjust the position of the monocrystal 1 in the direction of axis AA' and perpendicularly to this axis. The centre of the monocrystal 1 may thus be brought into the sphere of confusion of the goniometric device.

The sample-holder 8 is borne by a slave-goniometer 12 shown in greater detail in FIG. 3. This slave-goniometer 12 comprises a universal joint 14 mounted on a fixed base 15 which is fast with the frame of the apparatus. This support base may comprise two arms 15a, 15b, extending downwardly and between the lower ends of which is articulated, about a horizontal axis CC', a piece 16 forming part of the universal joint 14. This piece 16 may be in the form of an E and it may comprise a central arm 16a extending along axis CC' and two lateral arms 16b, 16c on the ends of which is rotatably mounted a circle 17, about an axis BB' perpendicular to axis CC'. This circle 17 presents, in its lower part, a chord 18 which extends parallel to axis BB' of rotation of the circle 17 with respect to the piece 16. This chord 18 is traversed by the rod 11 of the sample-holder 8, said rod abutting on a bearing fitted on the chord 18 and of which the lower end is engaged, in abutment, in a bearing provided in the circle 17. To ensure drive of the sample-holder 8 and of the monocrystal 1, the rod 11 is fast with a bar 19 of ferromagnetic material which extends transversely and is housed in the sector of the circle 17 defined between the latter and the chord 18. This bar may be constituted either by a small iron bar or by a bar magnet. It is smaller than the master magnet 7 and it lies in the magnetic field H produced by this master magnet, as may be seen in FIG. 2.

It is therefore seen from the foregoing description that the sample-holder 8 and the monocrystal 1 may rotate on themselves about the first axis AA', that their support, in the present case the circle 17, may rotate about the second axis BB' perpendicular to the first axis AA' and that the piece 16 constituting the support of circle 17 may in turn rotate about the third horizontal axis CC' defined by the fixed base 15, the three axes AA', BB' and CC' pratically intersecting inside a sphere of confusion, with a diameter of the order of 0.01 mm, inside which lies the centre of the monocrystal 1 undergoing study.

Thus, whatever the orientation of the magnetic field H produced by the master magnet 7, the slave bar 19 is aligned on the lines of force of this field and consequently occupies a position parallel to that of the master magnet 7. The force of magnetic attraction exerted between the master magnet 7 and the slave bar 19 ensures servo-control of the slave-goniometer by the movements of rotation of the control goniometer 4 through angles $\chi$ and $\omega$ whilst the force of magnetic coupling transmits the rotation of the master magnet 7 on itself, to the slave bar 19 which rotates through an angle $\phi'$ about the first axis AA'.

FIG. 5 materializes the various reference axes and the axes of rotation of the various elements constituting the slave-goniometer according to the invention. Ox, Oy and Oz constitute the reference of the laboratory where the device is located. This Figure also indicates the angles of rotation controlled by the slave-goniometer 12, namely angle $\phi'$ about the first axis AA', angle $\gamma$ about the second axis BB' and angle $\chi'$ about the third axis CC'. FIG. 5 also indicates the angles of rotation controlled by the control goniometer 4, i.e. angles $\phi$, $\chi$ and $\omega$.

In order not to interfere with the X-rays of the incident beam $f_i$, the third axis CC' is offset by an angle $\delta$ from the direction Ox which corresponds to that of the incident beam $f_i$.

With such a device, the monocrystal 1 may take all possible orientations, as in the case of a conventional assembly, whilst remaining in the incident X-ray beam $f_i$. Furthermore, the precision of positioning is obtained provided that the equilibrium of the slave-goniometer 12 is indifferent with respect to the three axes AA', BB', CC'.

Contrary to what is shown in FIG. 5, it is not absolutely necessary that the slave-goniometer 12 be associated with the control goniometer 4, with the result that the axes of rotation AA' and OG are strictly merged. In fact, if axis AA' is inclined by a small angle with respect to axis OG, the movement is such that any vector passing through O effects a movement of rotation about OG: it is therefore a movement of the same nature as that which this vector would have if axes AA' and OG merged. Introducing an angular shift between axes AA' and OG is the same as modifying the orientation of the crystal, which is of no consequence since the crystal is stuck along axis AA' with any orientation. This is particularly important, because, as a result, the only constraint to be respected, when the slave-goniometer 12 is associated with the control goniometer 4, is that their respective centres by merged.

In particular, it is not necessary for the master magnet 7 to be placed with a precision such that the lines of force of the magnetic field of this magnet are distributed symmetrically with respect to a plane passing through the axis OG and parallel to the magnetization, as well as by a plane passing through the axis OG and perpendicular to the magnetization.

FIG. 2 illustrates the use of the slave-goniometer according to the invention for studying the properties of a monocrystal at very low temperature. To this end, the slave-goniometer 12 is housed in a cryostat 21 so that the slave-goniometer 12 is separated from the master magnet 7 by the assembly of the walls of the cryostat which must naturally be made of a material permeable to the magnetic flux. The slave-goniometer 12 is fixed inside the cryostat 21 by means of a quartz tube 22 which presents a very low heat conductivity and a very low coefficient of expansion between 4K and 300K. In order to limit to a maximum the effects of contraction of the pieces constituting the goniometric device on the position of the crystal, the lower end of the quartz tube 22 is bonded as closely as possible to the crystal 1, therefore very close to the intersection of the three axes of rotation AA', BB' and CC'. In order to limit to a maximum the effects of expansion and of vibration of the cryostat 21 on the position of the crystal 1, the upper end of the quartz tube 22 is attached, outside the cryostat, to the frame of the diffractometer, via a device of the "xyz" type.

The magnetic coupling between the master magnet 7 and the slave bar 19 performs two functions and enables the precision of positioning to be increased.

The first function performed by the magnetic coupling is the movement of rotation about the first axis AA' (angle $\phi'$). To effect this coupling, the master magnet 7 must present the largest remanent field possible. It is preferably made of "ticonal" and its shape is chosen so that the field is as strong as possible in the vicinity of the driven slave bar 19. It is thus seen that the master magnet 7 is in the form of a parallelepipedic block extended, at its two polar ends, by polyhedral polar pieces 7a, 7b ensuring the concentration of the magnetic flux.

Furthermore, the driven slave bar 19 must present a very high magnetization. It may be advantageously constituted by soft material which acquires a very high magnetization in the presence of an external field.

The second function having to be performed by the magnetic coupling is the movement of translation along the circle 6 (angle $\chi$). To effect this coupling, the magnetic field created by the master magnet 7 must present a considerable gradient in directions Mx and Mz (FIG. 4) in order to compensate the imperfections in the system (frictions and possible slight unbalance). This is made by cutting sharp edges 7c, 7d in the iron polar pieces 7a, 7b. Furthermore, the driven slave bar 19 must present a very strong magnetization and it must be cut in the form of a needle.

What is claimed is:

1. An apparatus comprising a goniometric device particularly for X-ray or neutron diffractometry on monocrystals or any other sample comprising a sample-holder to maintain the monocrystal to be analyzed in the axis of the incident X-ray or neutron beam, means for driving this sample-holder on itself, about a first axis, and also in rotation about a second axis perpendicular to the first and a third axis perpendicular to the second, wherein the sample-holder is borne by a slave-goniometer comprising a transverse bar made of ferromagnetic material fast with the sample-holder, therefore perpendicular to the first axis of rotation of the sample-holder on itself, a support on which the sample-holder is rotatably mounted and which forms part of a universal joint mounted on a fixed base and of which the two perpendicular axes correspond respectively to the second and third axes of rotation, and means are provided for creating a magnetic field whose orientation varies in space so that, for each determined orientation of the magnetic field, the ferromagnetic bar and consequently the sample-holder and the monocrystal take this same orientation.

2. An apparatus according to claim 1, wherein the sample-holder and the slave-goniometer are housed in a tight enclosure, in particular that of a cryostat, and they are separated by a wall from the means producing the magnetic field whose orientation varies in space.

3. An apparatus according to claim 2, further comprising a diffractometer wherein the slave-goniometer is suspended from the lower part of a quartz tube which is fixed at its upper part to the frame of the diffractometer.

4. An apparatus according to claim 1 wherein the fixed base which is fast with the frame of the apparatus, comprises two arms extending downwardly and between the lower ends of which is articulated, about a third horizontal axis, a piece forming part of the universal joint, this piece being in the form of an E and comprising a central arm extending along the third axis and two lateral arms on the ends of which is rotatably mounted a circle, about a second axis perpendicular to the third axis.

5. An apparatus according to claim 4, wherein the circle presents, in its lower part, a chord which extends parallel to the second axis of rotation of the circle with respect to the piece, said chord being traversed by the sample-holder, and the bar of ferromagnetic material integral with the sample-holder is housed in the sector of the circle defined between the latter and the chord.

6. An apparatus according to claim 1 wherein the means creating the magnetic field whose orientation varies in space are constituted by a permanent magnet mounted to rotate on itself about the first axis.

7. An apparatus according to claim 6, wherein the permanent magnet is in the form of a parallelepipedic block extended, at its two polar ends, by polyhedral polar pieces cutted with sharp edges.

8. An apparatus according to claim 1, wherein the means creating the magnetic field with space-variable orientation are constituted by an assembly of coils disposed around the slave-goniometer and having currents of adjustable intensities passing therethrough, the elementary magnetic fields created by the different coils contributing to form a resultant magnetic field of variable orientation which controls the positon of the sample-holder.

9. An apparatus according to claim 1 wherein the sample-holder comprises a quartz rod on the upper end of which the monocrystal is stuck, this quartz rod being threaded in a tube filled with silicon grease and which in turn is screwed on the threaded upper end part of a rod materializing the axis of rotation of the sample-holder and of the monocrystal on themselves.

10. An apparatus comprising a goniometric device for x-ray or neutron diffractometry of a sample comprising:
(a) a sample-holder for maintaining said sample along an incident x-ray or neutron beam axis;
(b) means for rotating said sample-holder about a first axis lying along the length of said sample-holder, about a second axis perpendicular to said first axis, and about a third axis perpendicular to said second axis and said first axis;
(c) a slave-goniometer for carrying said sample-holder, said slave-goniometer comprising a transverse bar connected to said sample-holder perpendicular to said first axis; and
(d) means for creating a magnetic field having a variable spacial orientation such that for any spacial orientation of said magnetic field, said transverse bar, said sample-holder and said sample assume the same spacial orientation.

11. An apparatus according to claim 10 wherein said transverse bar comprises ferromagnetic material.

12. An apparatus according to claim 10 wherein said means for rotating said sample-holder comprises a support.

13. An apparatus according to claim 12 wherein said support comprises a portion of a universal joint, one of the two perpendicular axes of said universal joint lying along said second axis, and the other of the two perpendicular axes of said universal joint lying along said third axis.

14. An apparatus according to claim 13 further comprising a fixed base, wherein said universal joint is mounted on said fixed base.

* * * * *

UNITED STATES PATENT AND TRADEMARK OFFICE
CERTIFICATE OF CORRECTION

PATENT NO. : 4,658,411

DATED : April 14, 1987

INVENTOR(S) : Roger ARGOUD et al.

It is certified that error appears in the above-identified patent and that said Letters Patent is hereby corrected as shown below:

At column 2, line 1, change "positon" to ---position---.
At column 6, line 19 (i.e., in claim 8, line 8), change "positon" to ---position---.
At column 6, lines 30 and 32 (i.e., in claim 10, lines 2 and 4), change "x-ray" to ---X-ray---.

Signed and Sealed this

Fifth Day of July, 1988

Attest:

DONALD J. QUIGG

*Attesting Officer*  *Commissioner of Patents and Trademarks*